US012728100B2

(12) United States Patent
Kim et al.

(10) Patent No.: US 12,728,100 B2
(45) Date of Patent: Sep. 8, 2026

(54) METHOD OF PREPARING HYALURONIC ACID NANOPARTICLES

(71) Applicant: AMOREPACIFIC CORPORATION, Seoul (KR)

(72) Inventors: Hyuk Kim, Yongin-si (KR); Chaeyeon Song, Yongin-si (KR); Joonho Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 352 days.

(21) Appl. No.: 18/201,559

(22) Filed: May 24, 2023

(65) Prior Publication Data

US 2023/0381114 A1 Nov. 30, 2023

(30) Foreign Application Priority Data

May 26, 2022 (KR) ........................ 10-2022-0064855
May 12, 2023 (KR) ........................ 10-2023-0061856

(51) Int. Cl.

*A61K 9/51* (2006.01)
*A61K 8/02* (2006.01)
*A61K 31/728* (2006.01)

(52) U.S. Cl.

CPC .......... *A61K 9/5192* (2013.01); *A61K 8/0241* (2013.01); *A61K 31/728* (2013.01); *A61K 2800/413* (2013.01)

(58) Field of Classification Search

CPC .. A61K 9/5192; A61K 8/0241; A61K 31/728; A61K 2800/413
See application file for complete search history.

(56) References Cited

U.S. PATENT DOCUMENTS 8,467,868 B1 * 6/2013 Mohapatra ............. A61N 1/325 604/20
2014/0363568 A1 * 12/2014 Suematsu ............. H01M 4/625 427/123
2015/0024116 A1 * 1/2015 Matson ................... A61L 31/10 427/2.24
2021/0363329 A1 * 11/2021 Nishijima ................. C08L 1/02

FOREIGN PATENT DOCUMENTS

CN 112957277 A * 6/2021 ............. A61Q 19/00
CN 107998437 B 7/2021
JP 6752057 B2 * 9/2020
KR 10-2020-0048476 A 5/2020
KR 20200048476 A * 5/2020 ............. A61Q 19/00

OTHER PUBLICATIONS

Deformation and degradation of polymers using UHPD; accessed Jun. 2025 (Year: 2011).*
Machine translation of JP-6752057-B2 (Year: 2020).*
Machine translation of KR-20200048476-A (Year: 2020).*
Machine translation of CN-112957277-A (Year: 2021).*
High Molecular Weight Hyaluronic Acid (May 13, 2021 internet wayback machine); accessed Jun. 2025 (Year: 2021).*
Kondo et al.; Aqueous counter collision using paired water jets as a novel means ofpreparing bio-nanofibers; Elsevier; Carbohydrate Polymers 112 (2014) 284-290 (Year: 2014).*
Yu et al.; Preparation of carbon nanoparticles from activated carbon by aqueous counter collision; Springer Open; Journal of Wood Science (2022) 68:29 [published May 19, 2022] (Year: 2022).*

* cited by examiner

*Primary Examiner* — Robert A Wax
*Assistant Examiner* — John W Lippert, III
(74) *Attorney, Agent, or Firm* — Sughrue Mion, PLLC

(57) ABSTRACT

The present disclosure relates to a method for preparing hyaluronic acid nanoparticle and to hyaluronic acid nanoparticle prepared by the method. In one aspect of the present disclosure, the method for preparing hyaluronic acid nanoparticle can minimize the size of the hyaluronic acid nanoparticle, and the hyaluronic acid nanoparticle prepared by the method has low viscosity characteristics and is excellent in spreadability, and can penetrate the stratum corneum evenly when applied to the skin.

9 Claims, 9 Drawing Sheets

FIG. 11 purified water

Comparative Example 3

Example 7

Comparative Example 4

Example 8

METHOD OF PREPARING HYALURONIC ACID NANOPARTICLES

CROSS REFERENCE TO RELATED APPLICATION

The present application claims priority to Korean Patent Application Nos. 10-2022-0064855 filed on May 26, 2022 and 10-2023-0061856 filed on May 12, 2023, and the entire contents of which is incorporated herein for all purposes by this reference.

BACKGROUND OF THE INVENTION

Field of the Invention

The present specification relates to a method for preparing hyaluronic acid nanoparticles.

Description of the Related Art

Hyaluronic acid is a linear polysaccharide and is composed of D-glucuronic acid and N-acetylglucosamine. Hyaluronic acid is a natural substance that exists in the body and is widely used for medical purposes because it has no rejection or side effects and is less likely to cause pain or inflammation. Hyaluronic acid, which is a natural polymer, has begun to be used for ophthalmic surgery, and is widely used as an arthritis treatment agent, an adhesion inhibitor after surgery, and the like. In addition, since there are a large amount of carboxyl groups and hydroxyl groups in the molecule, the hyaluronic acid is hydrophilic and has excellent moisturizing effect, so it is widely employed in the cosmetic industry.

Since the hyaluronic acid undergoes rapid metabolism in the body by hyaluronidase, a degrading enzyme, high molecular weight hyaluronic acid is required to be used for a long time in the body as a biopolymer. However, since high molecular weight hyaluronic acid has high viscosity and poor mechanical properties and cannot pass through small skin barriers or pores, low molecular weight hyaluronic acid, which is more easily absorbed by the skin, is used together with high molecular weight hyaluronic acid in the cosmetic field.

Methods of reducing the molecular weight of hyaluronic acid include a decomposition method using gamma rays, a method using ultrasonic waves, a method using ultraviolet rays, a method using heat, a method using acid or alkali treatment, and a method using hyaluronic acid degrading enzymes. These methods are suitable for reducing the molecular weight of already manufactured high molecular weight hyaluronic acid, and there is a problem in that additional treatment and processes are required in reducing low molecular weight and cost increases. In addition, there is a disadvantage in that browning or by-products are generated during the hydrolysis process.

On the other hand, there is a method of preparing hyaluronic acid nanoparticles or crosslinked hyaluronic acid nanoparticles as a method for improving the skin absorption ability of high molecular weight hyaluronic acid that can be used for a long time in the body while overcoming the disadvantages of low molecular weight hyaluronic acid. It is known that uptake of macromolecules in nanoscale systems facilitates their penetration of the epithelial barrier and protects them from degradation. Methods for preparing hyaluronic acid nanoparticles include a method of inducing a polyion complex using an ionic material, a method of inducing self-assembly by introducing a hydrophobic moiety into hyaluronic acid, and a method of preparing cross-linked hyaluronic acid nanoparticles by physical methods such as emulsification, coacervation, spray drying, etc. adding a crosslinking agent in hyaluronic acid and chemical methods such as heterogeneous polymerization.

However, conventional methods for preparing hyaluronic acid nanoparticles, including the above methods, have a problem that the hyaluronic acid nanoparticles are not in the form of pure hyaluronic acid due to changes in the structure of hyaluronic acid through the introduction of hydrophobic residues, use of ionic substances, and organic solvents used as reaction catalysts in the preparing process, or use materials that are difficult to use as a cosmetic composition. In addition, there is a lot of loss in obtaining nanoparticles during the accompanying washing and drying process to remove organic solvents and by-products used in the preparing process, so it is difficult to design an efficient process, and the actual yield is only about 50 to 70%. In addition, in the case of hyaluronic acid nanoparticles prepared by this process, it is made of 0.01 to 0.1% hyaluronic acid, so there is a limit to preparing the hyaluronic acid particles in a concentration range applicable to cosmetics.

On the other hand, in order for active ingredients to be absorbed deep into the skin, the stratum corneum, which is the outermost layer of the epidermal layer of the skin, must be first penetrated, and the stratum corneum acts as the biggest barrier to absorption of external substances. The stratum corneum is composed of keratinized keratinocytes and lipid lamellar layers formed between these keratinocytes in a "brick and mortar" form. In general, it is known that permeation of efficacious substances through the lipid layer between skin keratinocytes (intercellular pathway) is more effective than permeation of efficacious substances into the skin directly through skin keratinocytes (transcellular pathway). Since the distance between keratinocytes in the stratum corneum is about several tens of nanometers, it is advantageous to control the particle size of nanoparticles to a size of 100 nm or less in order to pass the nanoparticles through the gap.

SUMMARY OF THE INVENTION

In one aspect, the present specification is to provide a method for preparing hyaluronic acid nanoparticles capable of minimizing the particle size of the nanoparticles.

In one aspect, the present specification provides a method for preparing hyaluronic acid nanoparticle, comprising crushing hyaluronic acid by aqueous counter collision.

In an exemplary embodiment, the aqueous counter collision may be performed under a pressure condition of 130 to 250 Mpa.

In an exemplary embodiment, the aqueous counter collision may be performed with a number of sprayings of 10 to 60.

In an exemplary embodiment, the aqueous counter collision may be performed with a nozzle having a diameter of 130 to 230 pin.

In an exemplary embodiment, the hyaluronic acid may comprise cross-linked hyaluronic acid.

In an exemplary embodiment, a molecular weight of the hyaluronic acid may be 500,000 to 2,000,000 Da.

In one aspect, the present specification provides a method for preparing hyaluronic acid nanoparticle, comprising performing nanoparticulation of hyaluronic acid by ultra-high pressure dispersion, wherein the ultra-high pressure dispersion is performed under a pressure condition of 130 to 250 Mpa.

In an exemplary embodiment, the ultra-high pressure dispersion may be performed repeatedly 10 to 60 times, In another aspect, the present specification provides the hyaluronic acid nanoparticle prepared by the method for preparing hyaluronic acid nanoparticle.

In one aspect, the method for preparing hyaluronic acid nanoparticle disclosed herein may provide hyaluronic acid nanoparticles having a minimized particle size.

In one aspect, the method for preparing hyaluronic acid nanoparticle disclosed herein may provide pure nano-sized hyaluronic acid particles without by-products.

In one aspect, the hyaluronic acid nanoparticles prepared according to the method for preparing hyaluronic acid nanoparticle disclosed herein have low viscosity and excellent spreadability.

In one aspect, the hyaluronic acid nanoparticles prepared according to the method for preparing hyaluronic acid nanoparticle disclosed herein may evenly penetrate the stratum corneum when applied to the skin.

BRIEF DESCRIPTION OF THE DRAWINGS

FIG. 11 shows a molecular weight distribution of cross-linked hyaluronic acid nanoparticles prepared by a method according to one embodiment of the present disclosure.

DETAILED DESCRIPTION OF THE INVENTION

Figure 1:
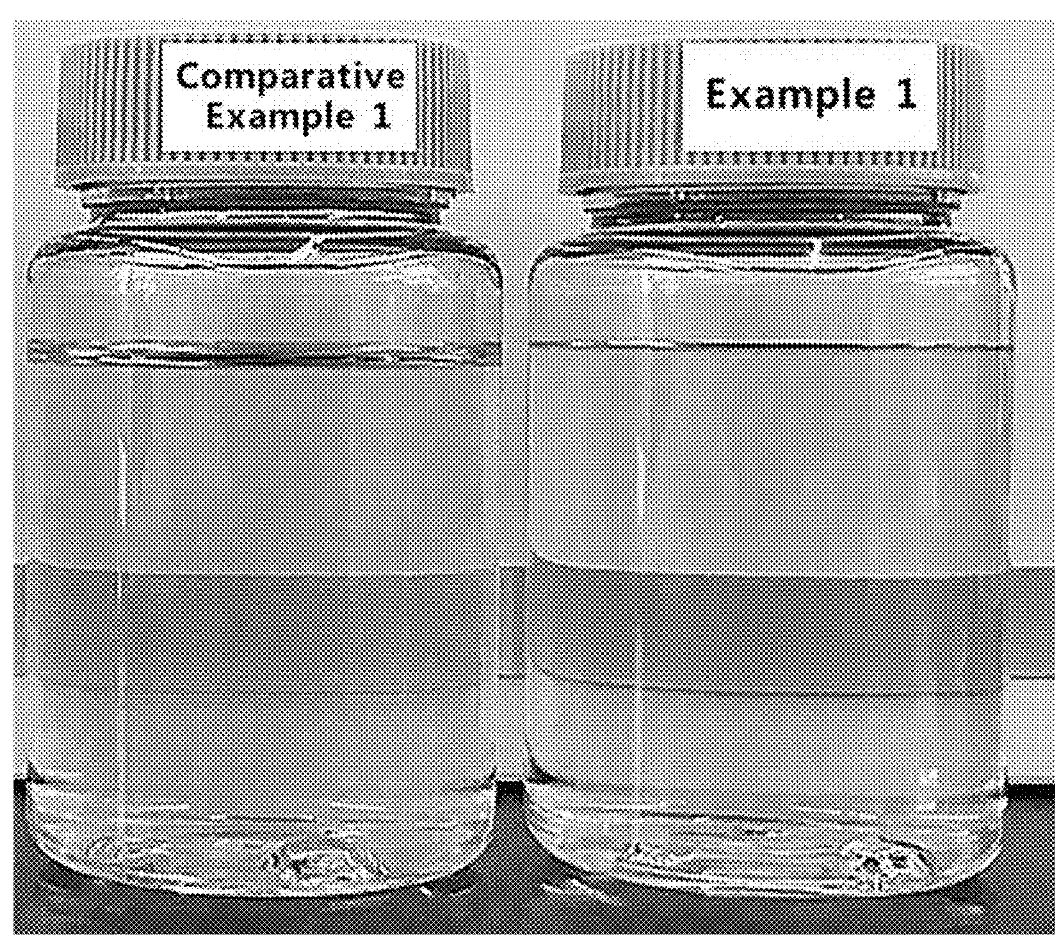
FIG. 1 shows a visual observation of an aqueous solution of hyaluronic acid nanoparticles according to one embodiment of the present disclosure.

As the terms used in the present specification, general terms which are currently widely used are adopted as much as possible in consideration of functions in the present disclosure. But, the terms may be changed depending on the intention of those skilled in the art, precedents, the emergence of new technology, etc. Further, in a specific case, a term arbitrarily selected by the applicant may be used and, in that case, the meaning of the term will be described in detail in the corresponding part. Accordingly, the terms used in the present disclosure should be defined based on not the name of the term but the meaning of the term and the contents throughout the present disclosure.

Unless defined otherwise, all the terms used herein, including technical or scientific terms, should have the same meanings as commonly understood by those having ordinary knowledge in the ad to which the present disclosure belongs. The commonly understood terms should be interpreted as having the meaning consistent with the meaning in the context of the related art, and should not be interpreted as being ideally or excessively formal unless they are defined clearly in the present disclosure.

A numerical range includes the numerical values defined in the present disclosure. Throughout the present specification, any maximum numerical limitation includes each lower numerical limitation, as if the lower numerical limitation were expressly written herein. Each numerical limitation given throughout the present specification includes each higher numerical limitation, as if the higher numerical limitation were expressly written herein. Each numerical limitation given throughout the present specification includes each narrower numerical range falling within a broader range, as if the narrower numerical range were expressly written herein.

As used herein, "comprising," "having," or "containing" is an inclusive or open-ended term that does not exclude elements or method steps that are not further recited. The term "or a combination thereof" as used herein refers to all sequences and combinations of the species listed before the above term. For example, "A, B, C or a composition thereof" is intended to include A, B. C, AB, AC, BC, or ABC and, where order is important on a particular context, at least one of BA, CA, CB, CBA, BCA, ACE, BAC, or CAB. Along with the above examples, iterative combinations containing more than one species or term are expressly included, e.g., BB, AAA, MB, BBC, AAABCCCC CBBAAA, CABABB, and the like. Those skilled in the art will understand that there is typically no limit to the number of items or terms in any combination, unless the context clearly dictates otherwise.

Hereinafter, the present disclosure will be described in detail.

In one aspect, the present disclosure provides a method for preparing hyaluronic acid nanoparticle comprising crushing hyaluronic acid by aqueous counter collision (ACC).

As used herein, the term "aqueous counter collision (ACC)" refers to a method of installing two or more nozzles facing each other and colliding solutions on both sides by spraying at high pressure. For example, the hyaluronic acid particles in the aqueous phase are cleaved by high-pressure collision to become hyaluronic acid nanoparticles. Since the temperature of the aqueous solution rises rapidly due to the collision, it can be cooled through a cooling system to maintain a constant temperature, and the size of the particles to be crushed may be controlled by adjusting the pressure, the number of spraying, the diameter of the nozzle, or the like.

In one embodiment, the aqueous counter collision may be performed under a pressure condition of 130 to 250 Mpa. For example, the pressure condition may mean the pressure of a cylinder for spraying a solution from a nozzle in the event of the aqueous counter collision. When the pressure condition of the aqueous counter collision is out of the above range, it becomes difficult to control the size of the hyaluronic acid nanoparticles. Specifically, the aqueous counter collision may be performed under the pressure condition of 130 Mpa or more, 135 Mpa or more, 140 Mpa or more, 145 Mpa or more, 150 Mpa or more, 250 Mpa or less, 245 Mpa or less, 240 Mpa or less, 235 Mpa or less, 230 Mpa or less, 225 Mpa or less, or 220 Mpa or less.

In one embodiment, the aqueous counter collision may be performed with a number of sprayings of 10 to 60. For example, the number of sprayings may mean the number of times a solution is sprayed from a nozzle and collides with each other in the event of the aqueous counter collision. If the number of sprayings is less than 10 times, the hyaluronic acid nanoparticles cannot be sufficiently refined, and if the number of sprayings is more than 60 times, manufacturing costs may increase due to spraying more than necessary. Specifically, the aqueous counter collision may be performed with a number of sprayings of 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 30 or more, 60 or less, 59 or less, 58 or less, 57 or less, 56 or less, 55 or less, 54 or less, 53 or less, 52 or less, 51 or less, 50 or less, 49 or less, 48 or less, 47 or less, 46 or less, 45 or less, 44 or less, 43 or less, 42 or less, 41 or less, or 40 or less.

In one embodiment, the aqueous counter collision may be performed with a nozzle having a diameter of 130 to 230 μm. If the diameter of the nozzle is less than 130 μm, the solution may not be sprayed smoothly, and if the diameter is greater than 230 μm, the particles may not be sufficiently refined. Specifically, the aqueous counter collision may be performed with a nozzle having a diameter of 130 μm or more, 133 μm or more, 135 μm or more, 137 μm or more, 140 μm or more, 143 μm or more, 145 μm or more, 147 μm or more, 150 μm or more, 153 μm or more, 155 μm or more, 157 μm or more, 160 μm or more, 230 μm or less, 227 μm or less, 225 μm or less, 223 μm or less, 220 μm or less, 217 μm or less, 215 μm or less, 213 μm or less, 210 μm or less, 207 μm or less, 205 μm or less, 203 μm or less, or 200 μm or less.

In one embodiment, the hyaluronic acid may include cross-linked hyaluronic acid.

In one embodiment, the molecular weight of the hyaluronic acid may be 500,000 to 2,000,000 Da. The physical properties of hyaluronic acid particles whose molecular weight is out of the above range may be deteriorated. For example, the molecular weight of the hyaluronic acid may be 500,000 Da or more, 550,000 Da or more, 600,000 Da or more, 650,000 Da or more, 700,000 Da or more, 750,000 Da or more, 800,000 Da or more, 850,000 Da or more, 900,000 Da or more, 2,000,000 Da or less, 1,950,000 Da or less, 1,900,000 Da or less, 1,850,000 Da or less, 1,800,000 Da or less, 1,750,000 Da or less, 1,700,000 Da or less, 1,650,000 Da or less, 1,600,000 Da or less, 1,550,000 Da or less, or 1,500,000 Da or less.

In one aspect, the present disclosure provides a method for preparing hyaluronic acid nanoparticle comprising performing nanoparticulation of hyaluronic acid by ultra-high pressure dispersion.

As used herein, the term "ultra-high pressure dispersion" refers to a method of dispersing particles contained in a fluid into fine particles by physically colliding the fluid using high pressure. For example, It may mean a method of cleaving particles in a fluid into fine sizes and dispersing them into nano-sized fine particles by spraying a fluid at high pressure through a nozzle. The size of the dispersed particles can be controlled by adjusting the pressure, number of repetitions, and diameter of the nozzle.

In one embodiment, the ultra-high pressure dispersion may be performed under a pressure condition of 130 to 250 Mpa. When the pressure condition of the ultra-high pressure dispersion is out of the above range, it becomes difficult to control the size of the hyaluronic acid nanoparticles. Specifically, the ultra-high pressure dispersion may be performed under a pressure condition of 130 Mpa or more, 135 Mpa or more, 140 Mpa or more, 145 Mpa or more, 150 Mpa or more, 250 Mpa or less, 245 Mpa or less, 240 Mpa or less, 235 Mpa or less, 230 Mpa or less, 225 Mpa or less, or 220 Mpa or less.

In one embodiment, the ultra-high pressure dispersion may be repeatedly performed 10 to 60 times. Here, the number of repetitions may mean the number of times a fluid is sprayed through a nozzle during the ultra-high pressure dispersion. For example, the ultra-high pressure dispersion may be repeatedly performed 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 30 or more, 60 or less, 59 or less, 58 or less, 57 or less, 56 or less, 55 or less, 54 or less, 53 or less, 52 or less, 51 or less, 50 or less, 49 or less, 48 or less, 47 or less, 46 or less, 45 or less, 44 or less, 43 or less, 42 or less, 41 or less, or 40 or less.

In one embodiment, the hyaluronic acid nanoparticles nanoparticulated by the ultra-high pressure dispersion may have an average particle size of 100 nm or less. For example, the hyaluronic acid nanoparticles nanoparticulated by the ultra-high pressure dispersion may have an average particle size of 100 nm or less, 99 nm or less, 98 nm or less, 97 nm or less, 96 nm or less, nm or less, 94 nm or less, 93 nm or less, 92 nm or less, 91 nm or less, 90 nm or less, 89 nm or less, 88 nm or less, 87 nm or less, 86 nm or less, 85 nm or less, 84 nm or less, 83 nm or less, 82 nm or less, 81 nm or less, 80 nm or less, 79 nm or less, 78 nm or less, 77 nm or less, 76 nm or less, 75 nm or less, 74 nm or less, 73 nm or less, 72 nm or less, 71 nm or less, 70 nm or less, 1 nm or more, 2 nm or more, 3 nm or more, 4 nm or more, 5 nm or more, 6 nm or more, 7 nm or more, 8 nm or more, 9 nm or more, 10 nm or more, 11 nm or more, 12 nm or more, 13 nm or more, 14 nm or more, 15 nm or more, 16 nm or more, 17 nm or more, 18 nm or more, 19 nm or more, or 20 nm or more.

In one embodiment, the chemical structure of the hyaluronic acid may not be changed before and after the ultra-high pressure dispersion. For example, the chemical structure of the hyaluronic acid may be maintained unchanged before and after the ultra-high pressure dispersion.

In one embodiment, the difference in molecular weight of the hyaluronic acid before and after the ultra-high pressure dispersion may be 100,000 Da or less. For example, the molecular weight of the hyaluronic acid may not be changed before and after the ultra-high pressure dispersion.

For example, the difference in molecular weight of the hyaluronic acid before and after the ultra-high pressure dispersion may be 100,000 Da or less, 50,000 Da or less, 40,000 Da or less, 30,000 Da or less, 20,000 Da or less, 10,000 Da or less, 5,000 Da or less, 3,000 Da or less, 1,000 Da or less, 500 Da or less, 100 Da or less, 50 Da or less, or 10 Da or less.

In one embodiment, the ultra-high pressure dispersion may be performed with a nozzle having a diameter of 130 to 230 μm. If the diameter of the nozzle is less than 130 μm, the fluid may not be smoothly sprayed, and if the diameter is greater than 230 μm, particles may not be sufficiently refined. Specifically, the ultra-high pressure dispersion may be performed with a nozzle having a diameter of 130 μm or more, 133 μm or more, 135 μm or more, 137 μm or more, 140 μm or more, 143 μm or more, 145 μm or more, 147 μm or more, 150 μm or more, 153 μm or more, 155 μm or more, 157 μm or more, 160 μm or more, 230 μm or less, 227 μm or less, 225 μm or less, 223 μm or less, 220 μm or less, 217 μm or less, 215 μm or less, 213 μm or less, 210 μm or less, 207 μm or less, 205 μm or less, 203 μm or less, or 200 μm or less.

The method for preparing hyaluronic acid nanoparticle according to one aspect of the present disclosure may provide pure nanoscale hyaluronic acid nanoparticles without by-products. In addition, in the method for preparing hyaluronic acid nanoparticle according to one aspect of the present disclosure, the hyaluronic acid nanoparticle may be prepared to be contained in high content, 1% or more of the total weight of hyaluronic acid.

In one aspect, the hyaluronic acid nanoparticle prepared by the method for preparing hyaluronic acid nanoparticle according to one aspect of the disclosure is provided.

The present disclosure will be explained in more detail with reference to the following examples. It will be obvious to those skilled in the art that these examples are merely for illustrative purposes and the scope of the invention is not to be construed as being limited thereto.

Example 1: Preparation of Hyaluronic Acid Nanoparticles

An aqueous solution of hyaluronic acid was prepared by mixing sodium hyaluronate (Mw: 1000 kDa) in purified water at a concentration of 1.5% (w/v) for 3 hours. The aqueous solution of hyaluronic acid was subjected to nano-minimization under the conditions of a pressure of 200 MPa, a nozzle diameter of 180 nm, and the number of sprayings of 50 times using the aqueous counter collision (ACC) equipment to prepare hyaluronic acid nanoparticles.

Comparative Example 1

An aqueous solution of hyaluronic acid was prepared by mixing sodium hyaluronate (Mw: 1000 kDa) in purified water at a concentration of 1.5% (w/v) for 3 hours.

Figure 2:
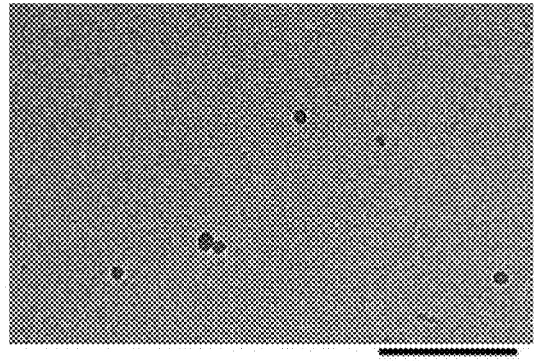
FIG. 2 shows an observation of hyaluronic acid nanoparticles prepared by a method according to one embodiment of the present disclosure with a transmission electron microscope.
Figure 3:
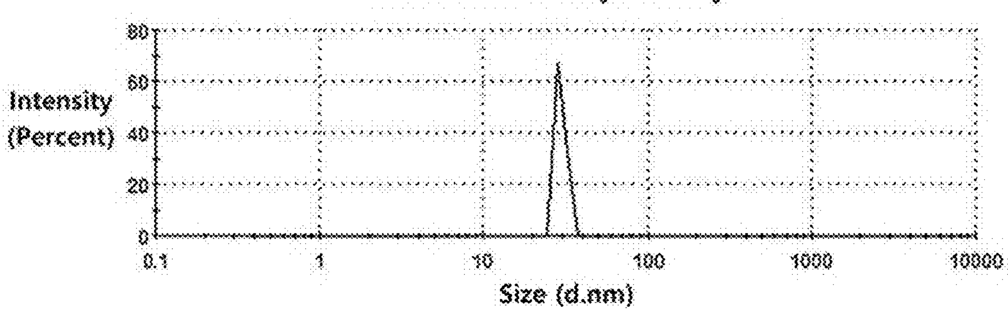
FIG. 3 shows a result of measuring the size of hyaluronic acid nanoparticles prepared by a method according to one embodiment of the present disclosure with a particle size analyzer.

[Experimental Example 1] Particle Size Analysis of Hyaluronic Acid Nanoparticles Transparency of Example 1 and Comparative Example 1 was visually observed and shown in FIG. 1. Referring to FIG. 1, it was confirmed that the blue line (thick line) on the rear side in Example 1 was more clearly visible than that in Comparative Example 1. In addition, the size of the particles of Example 1 was observed with a transmission electron microscope (TEM, JEM 3010, JEOL, Japan) and shown in FIG. 2, measured using a particle size analyzer (Nanobrook omni particle size analyzer, Malvern Panalytical), and shown in Table 1 and FIG. 3. In Table 1, the production yield was calculated as the difference between the input amount and the yield amount in the treatment process of aqueous counter collision.

TABLE 1

| | Pressure (Mpa) | Nozzle diameter (μm) | Number of sprayings | Average particle size (nm) | Production yield |
|---|---|---|---|---|---|
| Example 1 | 200 | 180 | 50 | 29.68 ± 2.09 | 96% |

As can be seen from the results of Experimental Example 1, in the case of Example 1 using the aqueous counter collision, it was confirmed that hyaluronic acid nanoparticles having a size of 100 nm or less were prepared, and the production yield was 96%, which was excellent.

Example 2: Preparation of Cross-Linked Hyaluronic Acid Nanoparticles

An aqueous solution of 20% (w/v) hyaluronic acid was prepared by adding sodium hyaluronate (Mw: 1000 kDa) to a 0.24N NaOH aqueous solution. Poly(ethylene glycol) diglycidyl ether (PEGDE, Sigma Aldrich), a cross-linking agent, was added to the aqueous solution of hyaluronic acid in an amount of 10% by weight of hyaluronic acid, followed by reaction at 37° C. for 24 hours to complete the cross-linking reaction. The crosslinked hyaluronic acid was sufficiently swollen with purified water and then pulverized to a size of 100 μm. The degree of water swelling was calculated by the formula "degree of swelling (times) =weight of swollen cross-linked hyaluronic acid/weight of dried cross-linked hyaluronic acid", and as a result, the degree of swelling of the prepared cross-linked hyaluronic acid was 65 times. The pulverized cross-linked hyaluronic acid was subjected to nano-minimization using the aqueous counter collision (ACC) equipment under the conditions of a pressure of 200 MPa, a nozzle diameter of 180 μm, and a number of sprayings of 10 times to prepare cross-linked hyaluronic acid nanoparticles.

Example 3

Crosslinked hyaluronic acid nanoparticles of Example 3 were prepared in the same manner as in Example 2, but the number of sprayings was 30 times.

Example 4

Crosslinked hyaluronic acid nanoparticles of Example 4 were prepared in the same manner as in Example 2, but the number of sprayings was 50 times.

Comparative Example 2

An aqueous solution of 20% (w/v) hyaluronic acid was prepared by adding sodium hyaluronate (Mw: 1000 kDa) to an aqueous solution of 0.24N NaOH, and poly(ethylene glycol) diglycidyl ether (PEGDE, Sigma Aldrich), a cross-linking agent, was added to the aqueous solution of hyaluronic acid in an amount of 10% by weight of hyaluronic acid. After the solution was reacted at 37° C. for 24 hours to complete the crosslinking reaction, the cross-linked hyaluronic acid was sufficiently swollen with purified water and pulverized to a size of 100 μm to prepare an aqueous solution of crosslinked hyaluronic acid.

Figure 4:
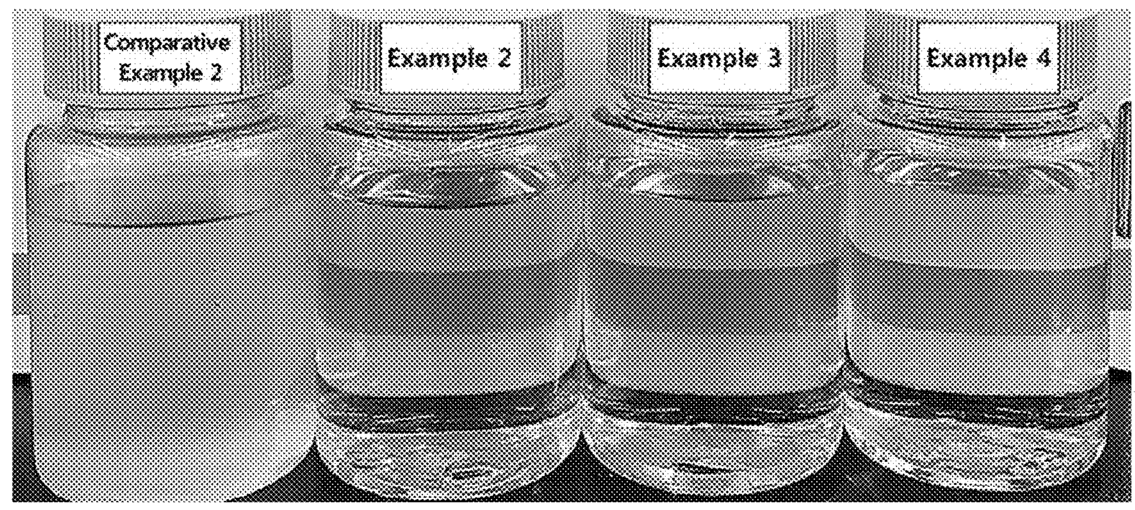
FIG. 4 shows a visual observation of an aqueous solution of cross-linked hyaluronic acid nanoparticles according to one embodiment of the present disclosure.
Figure 5:
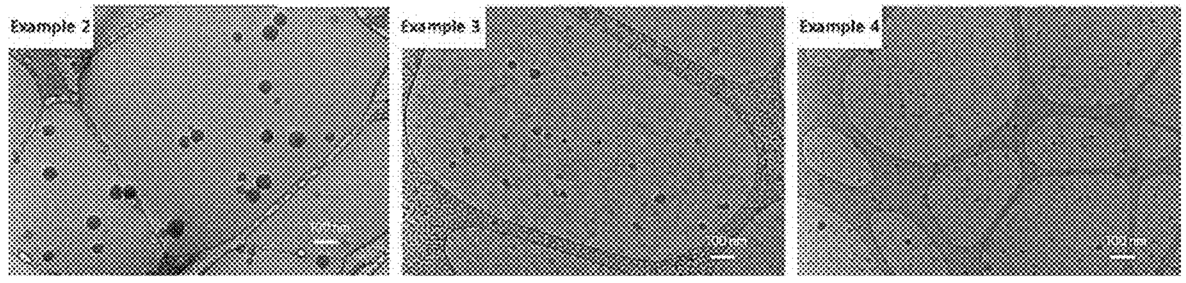
FIG. 5 shows an observation of cross-linked hyaluronic acid nanoparticles prepared by a method according to one embodiment of the present disclosure with a transmission electron microscope.
Figure 6:
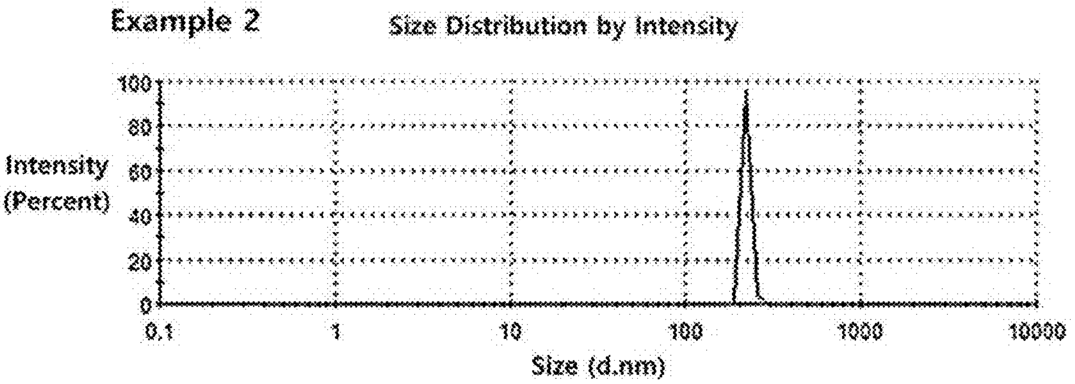
FIG. 6 shows a result of measuring the size of cross-linked hyaluronic acid nanoparticles prepared by a method according to one embodiment of the present disclosure with a particle size analyzer.
Figure 6:
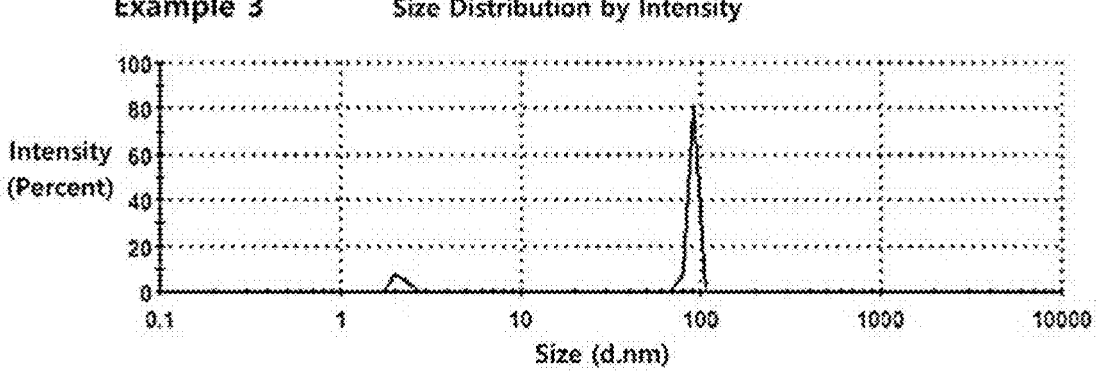
Figure 6:
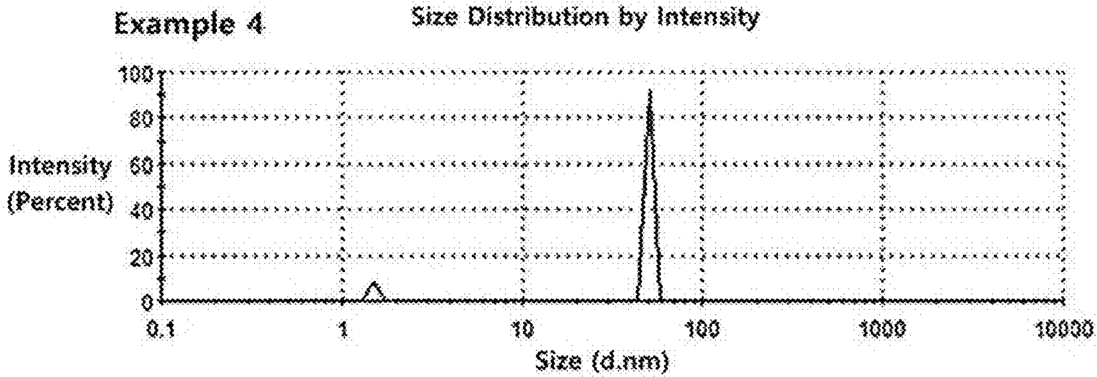

[Experimental Example 2] Particle Size Analysis of Cross-Linked Hyaluronic Acid Nanoparticles Transparency of Examples 2 to 4 and Comparative Example 2 was visually observed and shown in FIG. 4. Referring to FIG. 4, it was confirmed that the blue line (thick line) on the rear side in Examples 2 to 4 was clearly visible, whereas the blue line (thick line) on the rear side in Comparative Example 2 was almost invisible. In addition, the particles of Examples 2 to 4 were observed with a transmission electron microscope (TEM, JEM 3010, JEOL, Japan) and shown in FIG. 5, and the particle sizes of Examples 2 to 4 and Comparative Example 2 were measured using a particle size analyzer (Nanobrook omni particle size analyzer, Malvern Panalytical) and shown in Table 2 and FIG. 6. In Table 2, the production yield was calculated as the difference between the input amount and the yield amount in the treatment process of aqueous counter collision.

TABLE 2

| | Pressure (Mpa) | Nozzle diameter (μm) | Number of sprayings | Average particle size (nm) | Production yield |
|---|---|---|---|---|---|
| Comparative Example 2 | — | — | — | 116040 | — |
| Example 2 | 200 | 180 | 10 | 221.75 ± 1.01 | >95% |
| Example 3 | 200 | 180 | 30 | 90.25 ± 3.43 | >95% |
| Example 4 | 200 | 180 | 50 | 50.75 ± 1.01 | >95% |

[Experimental Example 3] Particle Size Analysis by Pressure

In order to analyze the particle size according to the pressure conditions of the aqueous counter collision, Examples 5 to 6 and Comparative Examples 3 to 4 were prepared in the same way as in Example 2, but the pressure and number of sprayings were set to the conditions shown in Table 3.

TABLE 3

| | Pressure (Mpa) | Nozzle diameter (μm) | Number of sprayings | Average particle size (nm) |
|---|---|---|---|---|
| Comparative Example 3 | 100 | 180 | 10 | 3642 ± 459 |
| Comparative Example 4 | 100 | 180 | 50 | 1185 ± 128 |
| Example 5 | 150 | 180 | 130 | 716 ± 74 |
| Example 6 | 150 | 180 | 50 | 82.8 ± 5.84 |

Figure 7:
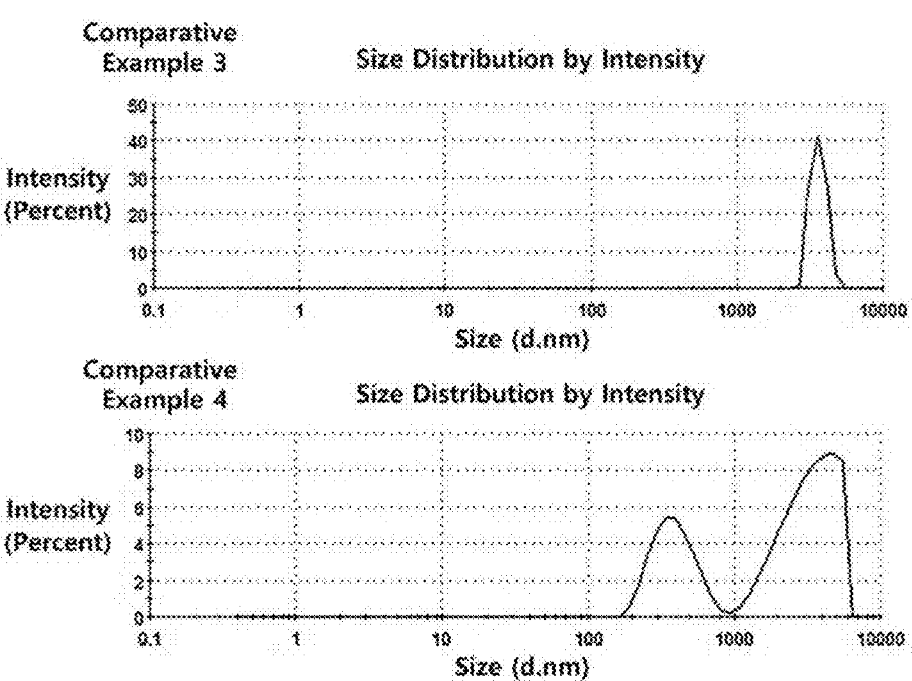
FIG. 7 shows a result of measuring the size of hyaluronic acid nanoparticles prepared by a method according to one embodiment of the present disclosure with a particle size analyzer.
Figure 7:
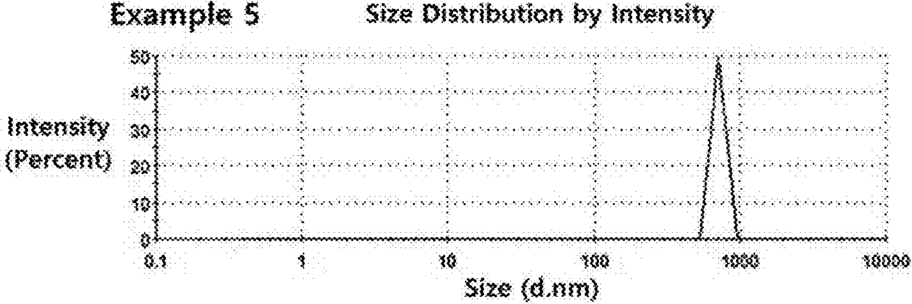
Figure 7:
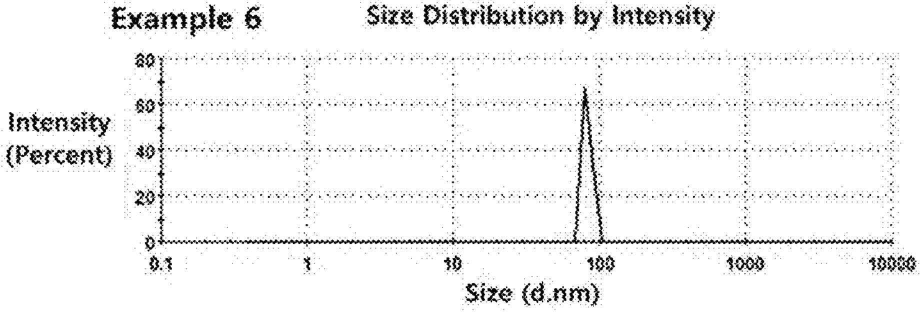

The particle sizes of Examples 5 to 6 and Comparative Examples 3 to 4 were measured using a particle size analyzer (Nanobrook omni particle size analyzer, Malvern Panalytical), and the results were shown in Table 3 and FIG. 7.

As can be seen in Table 3 and FIG. 7, Comparative Examples 3 and 4 prepared under the pressure condition of 100 Mpa did not produce nano-scale particles, whereas in Examples 5 and 6, hyaluronic acid nanoparticles were confirmed.

[Experimental Example 4] Analysis of Rheological Properties of Hyaluronic Acid Nanoparticles Changes in viscoelastic properties of Examples 1 to 4 and Comparative Examples 1 to 2 were measured using a rheometer (KINEXUS Pro+, USA). As for the measurement conditions, elasticity (storage modulus, G') and viscosity (loss modulus, G") were measured in a frequency range of 0.1 to 10 Hz, 1 Pa shear stress, and 1 mm gap using a 20 mm plate at 25° C. The results were shown in Table 4 by comparison with G', G", and Tan δ values at 1 Hz, and the Tan δ value was calculated according to the formula: Tan δ=G"IG'.

TABLE 4

| | G' (Pa@1Hz) | G" (Pa@1Hz) | Tanδ (G"/G') |
|---|---|---|---|
| Example 1 | 0.615 | 0.28 | 0.45 |
| Example 2 | 0.12 | 0.25 | 2.08 |
| Example 3 | 0.05 | 0.11 | 2.20 |
| Example 4 | 0.02 | 0.05 | 2.50 |
| Comparative Example 1 | 71 | 60 | 0.84 |
| Comparative Example 2 | 517 | 519 | 1.00 |

As shown in Table 4, compared to Comparative Examples 1 and 2, in Examples 1 to 4, it was confirmed that the viscoelasticity was greatly reduced to have low viscosity characteristics.

[Experimental Example 5] Analysis of the Chemical Structure of Hyaluronic Acid Nanoparticles Examples 1, 3 and 4 and Comparative Examples 1 and 2 were analyzed using Fourier Transform Infrared (FTIR) to determine the change in chemical structure of the hyaluronic acid nanoparticles due to the aqueous counter collision treatment. FTIR (NICOLET iS50, Thermo fisher scientific, USA) was measured in attenuated total reflection (ATR) mode, and the results were shown in FIGS. 8 and 9.

Figure 8:
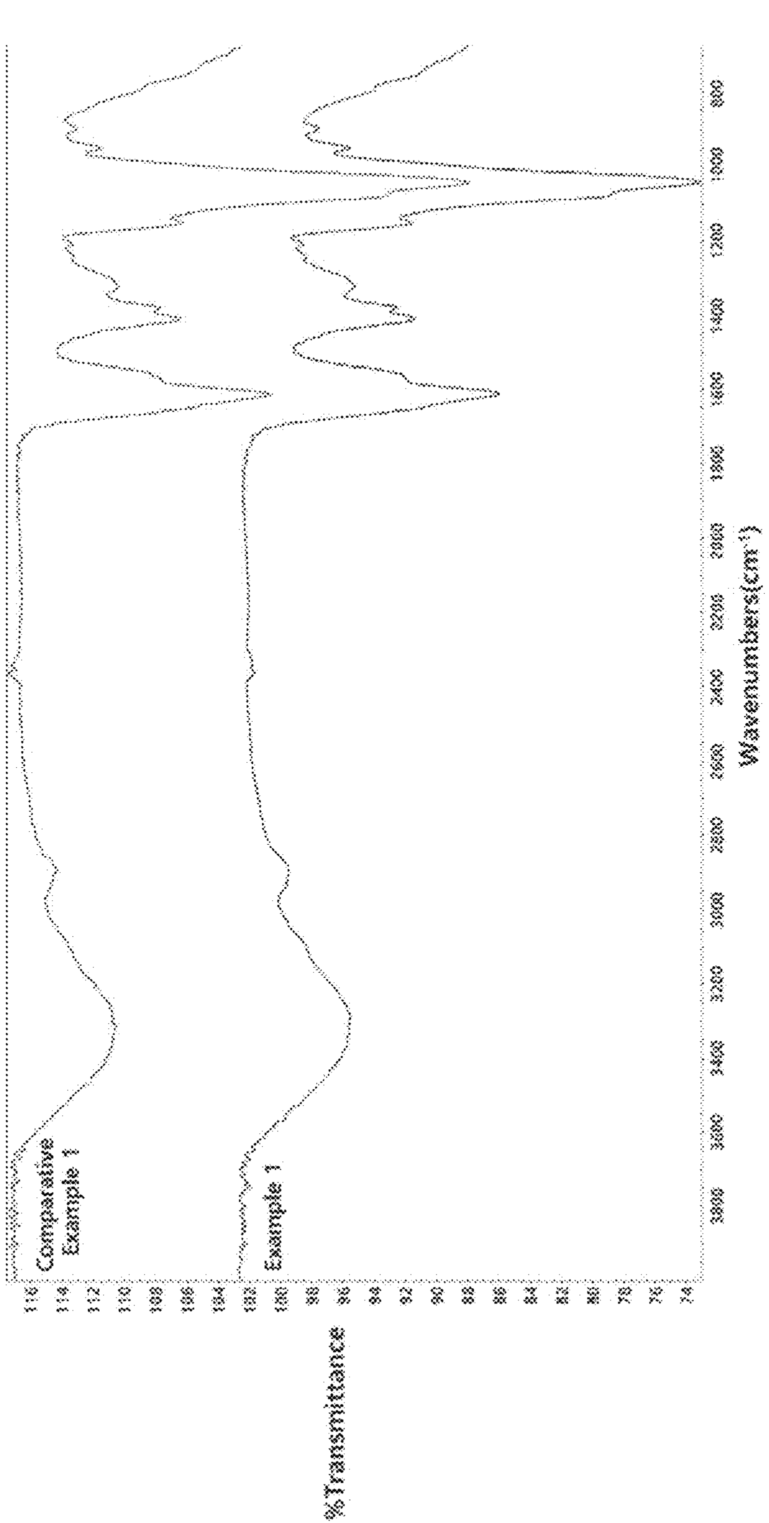
FIG. 8 shows an FTIR spectrum of hyaluronic acid nanoparticles prepared by a method according to one embodiment of the present disclosure.
Figure 9:
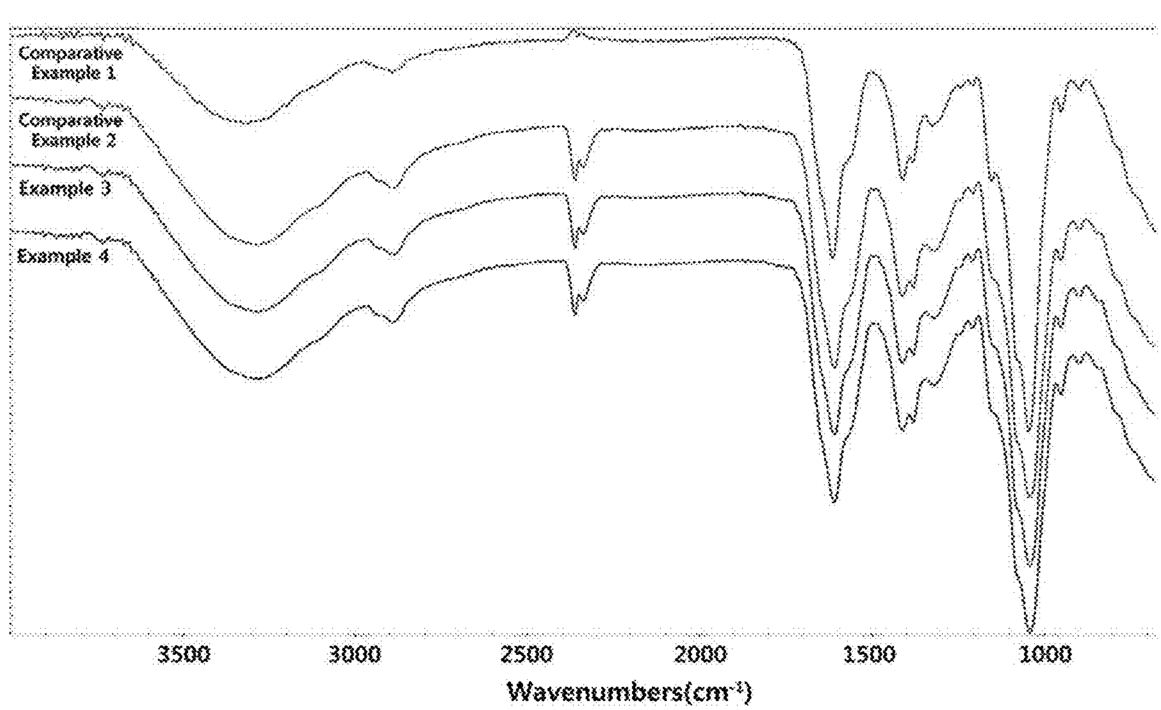
FIG. 9 shows an FTIR spectrum of cross-linked hyaluronic acid nanoparticles prepared by a method according to one embodiment of the present disclosure.

As can be seen from the results in FIG. 8, the FTIR spectrum of the nanoparticles of hyaluronic acid of Example 1 was found to be consistent with that of Comparative Example 1, indicating that the chemical structure of hyaluronic acid remained unchanged even after the aqueous counter collision treatment. In addition, as shown in FIG. 9, an ether bond was observed around 1108 $cm^{-1}$ as a specific absorption peak of cross-linked hyaluronic acid, and the FTIR spectra of Examples 3 and 4 also showed the specific absorption of cross-linked hyaluronic acid consistent with that of Comparative Example 2. It was found that the chemical structure of the cross-linked hyaluronic acid remained unchanged even after the aqueous counter collision treatment.

[Experimental Example 6] Molecular Weight Analysis of Hyaluronic Acid Nanoparticles If the changes in monomolecular structure of HA and CLHA were confirmed through FT-IR, the molecular weights of Comparative Example 1, Example 1, and Example 4 were analyzed using agarose gel electrophoresis to determine the change in polymer structure. Each sample was electrophoresed on a 1 agarose gel at a voltage of 35 V for 4 hours, then stained with 0.005% Stains-All (Sigma-Aldrich) for 24 hours and desalted in 30% ethanol until a distinct band was seen, and the results were shown in FIGS. 10 and 11. Molecular weights were compared using Select-HATM LoLadder (Echelon Biosciences Inc., USA) and LMW-HA (<50 kDa, Hyundai Bioland) was used as a control.

Figure 10:
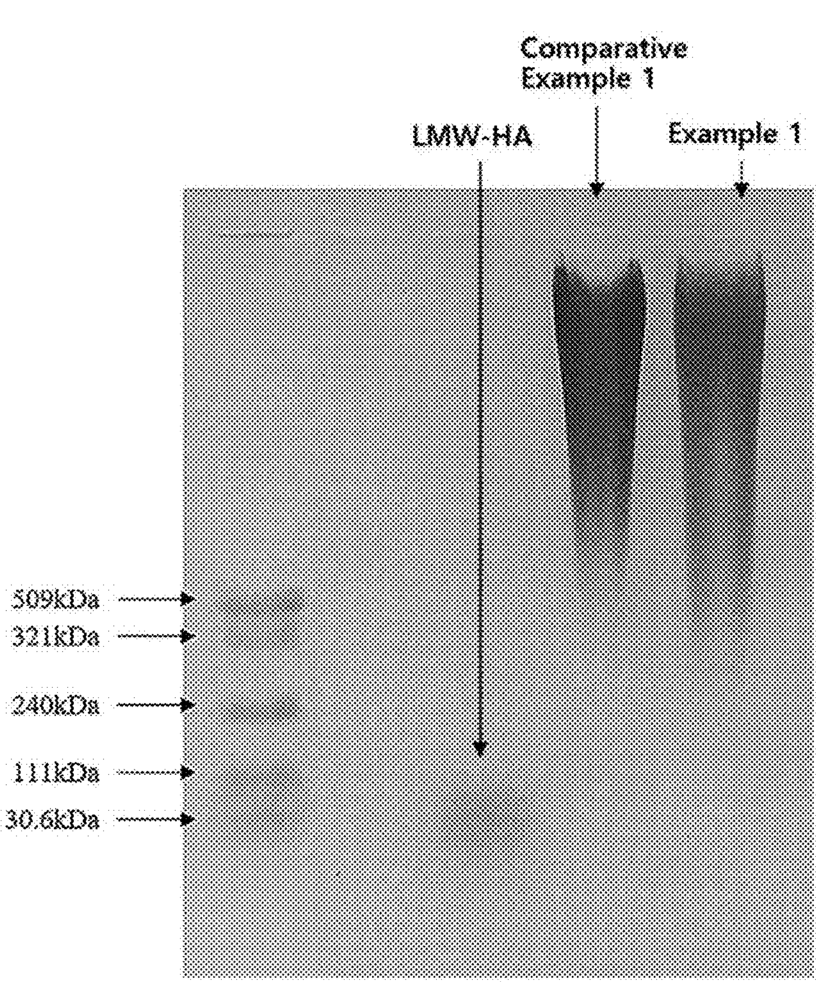
FIG. 10 shows a molecular weight distribution of hyaluronic acid nanoparticles prepared by a method according to one embodiment of the present disclosure.
Figure 11:
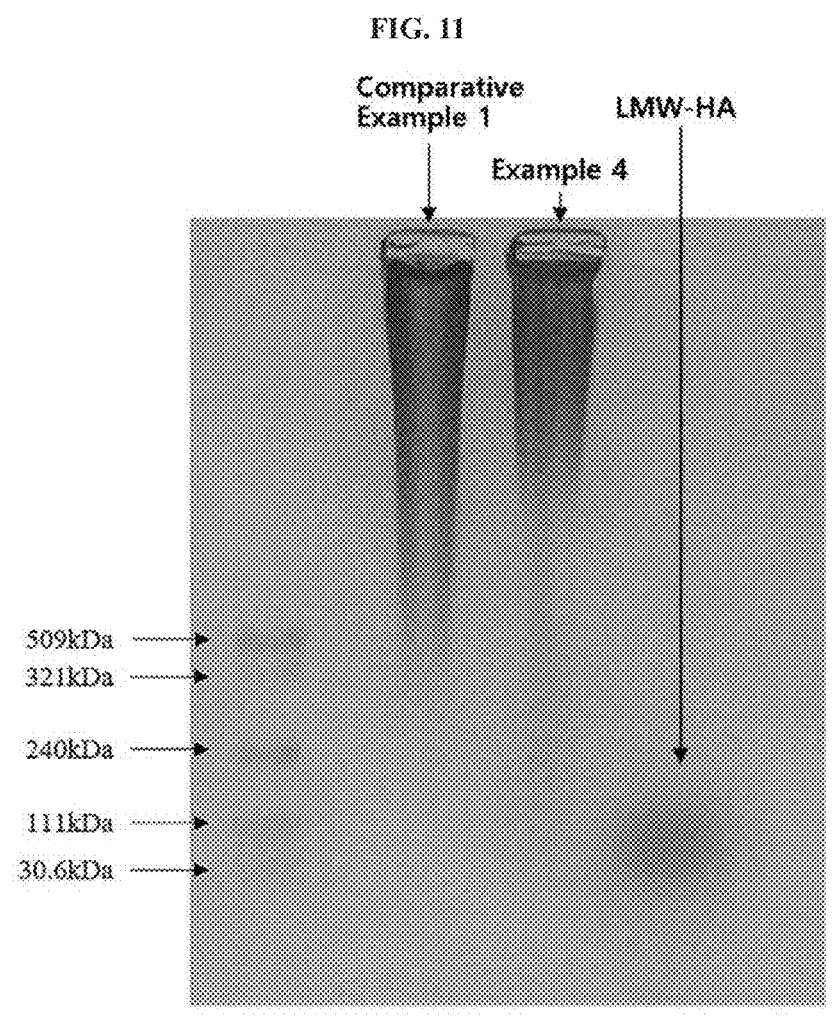

As can be seen from the results in FIG. 10, Example 1 showed a molecular weight distribution similar to that of Comparative Example 1, and maintained a higher molecular weight than that of LMW-HA. That is, it was found that the molecular weight of hyaluronic acid was maintained unchanged even after the aqueous counter collision treatment. In addition, as shown in FIG. 11, Example 4 was found to maintain a higher molecular weight compared to that of Comparative Example 1 because HA was in a chemically cross-linked form. That is, it was found that the chemically cross-linked structure was well maintained even after the aqueous counter collision treatment.

Example 7

Hyaluronic acid nanoparticles were prepared in the same manner as in Example 1, but sodium hyaluronate was replaced with fluorescent labeled hyaluronic acid (Mw: 640 to 1000 kDa, Sigma-Aldrich).

Example 8

Cross-linked hyaluronic acid nanoparticles were prepared in the same manner as in Example 4, but sodium hyaluronate was replaced with fluorescent labeled hyaluronic acid (Mw: 640 to 1000 kDa, Sigma-Aldrich).

Comparative Example 3

Fluorescein labeled hyaluronic acid (Mw: 640 to 1000 kDa, Sigma-Aldrich) was mixed with purified water at a concentration of 1.5% (w/v) for 3 hours to obtain an aqueous solution of hyaluronic acid, instead of sodium hyaluronate.

Comparative Example 4

A cross-linked hyaluronic acid solution was prepared in the same manner as in Comparative Example 2, but replacing sodium hyaluronate with fluorescent labeled hyaluronic acid (Mw: 640 to 1000 kDa, Sigma-Aldrich).

[Experimental Example 7] Evaluation of Skin Absorption of Hyaluronic Acid Nanoparticles Using the skin extracted from the cadaver skin, a skin absorption test was conducted for 24 hours through a Franz-cell device. In order to apply Examples 7 and 8 and Comparative Examples 3 and 4 to skin tissue, Examples 7 and 8 and Comparative Examples 3 and 4 were diluted 2-fold in PBS. Then, a certain amount of each of Examples 7 and 8 and Comparative Examples 3 and 4 was applied to skin tissue, left for 24 hours, and then the skin tissue was separated from Franz-cell to prepare sections for microscopic observation. The sections were observed using a fluorescence microscope and the results were shown in FIG. 12.

Figure 12:
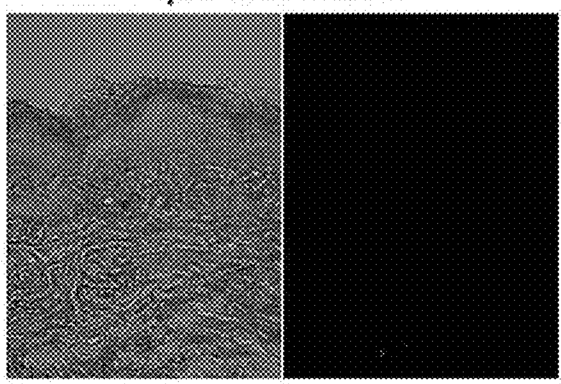
FIG. 12 shows a result of evaluating a skin absorption ability of hyaluronic acid nanoparticles prepared by a method according to one embodiment of the present disclosure.
Figure 12:
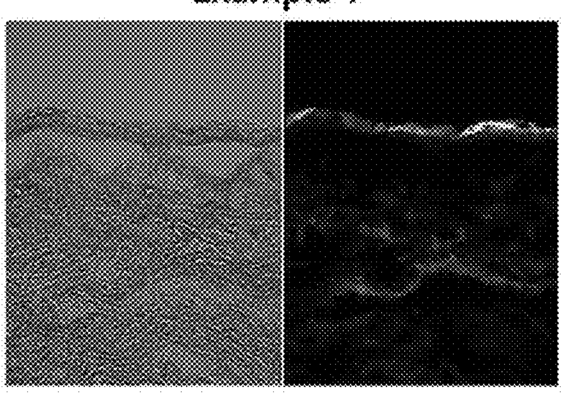
Figure 12:
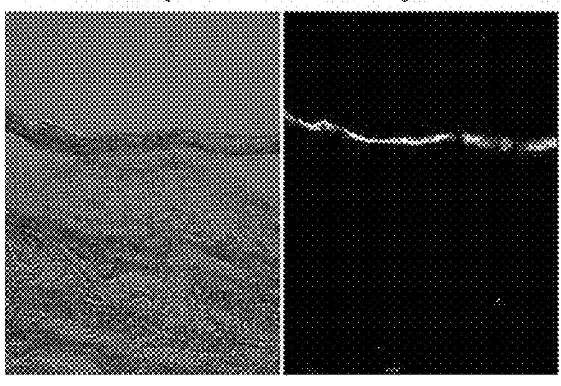
Figure 12:
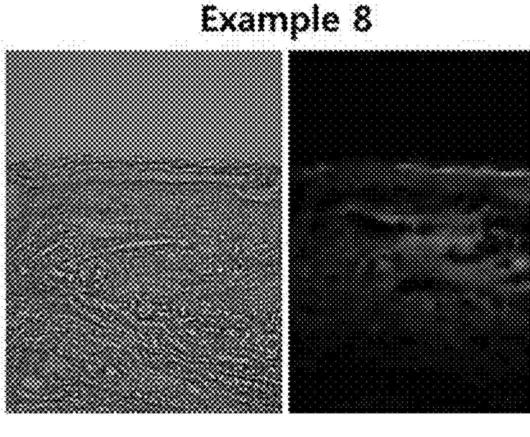

As can be seen in FIG. 12, in the case of Examples 7 and 8, it was confirmed that the fluorescent material, fluorescein (bright part), was evenly dispersed in the epidermal layer of the skin tissue, which confirming that the skin absorption of Examples 7 and 8 was well achieved.

What is claimed is:

1. A method for preparing a skin penetration formulation comprising hyaluronic acid nanoparticles, comprising performing nanoparticulation of a starting hyaluronic acid by a ultra-high pressure dispersion to obtain the hyaluronic acid nanoparticles, wherein the ultra-high pressure dispersion is performed under a pressure condition of 130 to 250 MPa, wherein a molecular weight of the starting hyaluronic acid and a molecular weight of hyaluronic acid of the hyaluronic acid nanoparticles have a difference of 100,000 Da or less, and wherein the ultra-high pressure dispersion is performed repeatedly 11 or more times.

2. The method of claim 1, wherein the ultra-high pressure dispersion is performed repeatedly 60 or less times.

3. The method of claim 1, wherein the ultra-high pressure dispersion is performed by crushing the starting hyaluronic acid by aqueous counter collision.

4. The method of claim 3, wherein the aqueous counter collision is performed with a nozzle having a diameter of 130 to 230 μm.

5. The method of claim 1, wherein the starting hyaluronic acid comprises a cross-linked hyaluronic acid.

6. The method of claim 1, wherein the molecular weight of the starting hyaluronic acid is 500,000 to 2,000,000 Da.

7. The method of claim 1, wherein the hyaluronic acid nanoparticles have an average particle size of 100 nm or less.

8. The method of claim 1, wherein the hyaluronic acid has no change in its chemical structure before and after the ultra-high pressure dispersion.

9. The skin penetration formulation prepared by the method of claim 1, wherein the hyaluronic acid nanoparticles have an average particle size of 100 nm or less.

* * * * *